United States Patent [19]

Hogan

[11] Patent Number: 6,028,187
[45] Date of Patent: Feb. 22, 2000

[54] **NUCLEIC ACID PROBES TO *LISTERIA MONOCYTOGENES***

[75] Inventor: James J. Hogan, Coronado, Calif.

[73] Assignee: Gen-Probe Incorporated, San Diego, Calif.

[21] Appl. No.: 08/486,534

[22] Filed: Jun. 7, 1995

Related U.S. Application Data

[63] Continuation of application No. 08/158,168, Nov. 24, 1993, abandoned, which is a continuation of application No. 07/739,644, Aug. 1, 1991, abandoned.

[51] Int. Cl.$^7$ .............................. C07H 21/04; C12Q 1/68
[52] U.S. Cl. .................................... 536/24.32; 536/24.33; 435/6
[58] Field of Search .............................. 435/6; 536/24.32, 536/24.33; 935/77, 78, 8

[56] References Cited

U.S. PATENT DOCUMENTS

| | | | |
|---|---|---|---|
| 4,689,295 | 8/1987 | Taber et al. ................................ | 435/6 |
| 5,030,557 | 7/1991 | Hogan ........................................ | 435/6 |
| 5,089,386 | 2/1992 | Stackebrandt .............................. | 435/6 |

FOREIGN PATENT DOCUMENTS

| | | |
|---|---|---|
| 3138784 | of 1985 | Australia . |
| 0155359 | of 1983 | European Pat. Off. . |
| 0133671 | 8/1984 | European Pat. Off. . |
| 0250662 | 8/1986 | European Pat. Off. . |
| 0232085 | of 1987 | European Pat. Off. . |
| 0245129 | of 1987 | European Pat. Off. . |
| 0277237 | of 1987 | European Pat. Off. . |
| 0314294 | 5/1989 | European Pat. Off. . |
| WO8301073 | of 1983 | WIPO . |
| WO8402721 | of 1984 | WIPO . |
| 8803957 | 6/1988 | WIPO . |

OTHER PUBLICATIONS

Collins, M.D. et al. Intern J Systemic Bacter. (Apr. 1991) 41:240–246.
Arnold et al Clin Chem (1989) 35:1588–1594.
Goodfellow and Minikin, "The Mycobacteria" Kubica and Wayne, eds., Dekker, 1984.
Mordorski et al., "Ribosomal Ribonucleic Acid Similarities in the Classification of Rhodococcus and Related Taxo" 118 J. Gen. Microbiol. 313 1980.
Goodfellow and Wayne, I "The Biology of the Mycobacteria" 476 1982.
Baess, "Deoxyribonucleic Acid Relationships Between Different Seovars of Miavium, M. intracellulare, and M.scrofulaceum" 91 Immunol. Scand. Sect. B 201 1983.
Bradley, "Relationships Among Mycobacteria and Nocardiae Based Upon Deoxyribonucleic Acid Reassociation" 113 J. Bacteriology 645, 1973.
Rogers et. al., "Construction of the Mycoplasma Evolutionary Tree from 5S.RNA Sequence Data" 82 Proc. Natl. Acad. Sci. USA 1160, 1986.
Yogev and Razin, "Common Deoxyribonucleic Acid Seqences in *Mycoplasma geritalium* and *Mycoplasma pneumoniae* Genomes" 36 Intnatl. J. Systemic Bact. 426, 1986.
Razin, Molecular and Biological Features of Mollicutes (Mycoplasmas) 135 Ann. Microbiol. 9, 1984.
Gobel et al., "Oligonucleotide Probes Complementary to Variable Regions of rRNA Discriminate Between Mycoplasma sp." 133 J. Gen. Microbiol. 1969, 1987.
Gobel "Cloned Mycoplasma rRNA Genes for the Detection of Mycoplasma Contamiation in Tissue Cultures" 226 Science 1211, 1984.
Razin "Molecular Biology and Genetics of Mycoplasmas" 49 Microbiol. Rev. 437, 1985.
Jones and Collins "Irregular, Nonsporing Gram Positive Rods" Bergey's Manual of Systemic Bacteriology, 1261 1986.
Boddinghaus et al. "Detection and Identification of Mycobacteria by Amplification of rRNA" 28 J. Clin. Micro. 1751, 1990.
Rogall et al. "Differentiation of Mycobacterium sp. by Direct Sequencing of Amplified DNA" 136 J. Gen. Micro. 1915 1990.
Rogall et al "Towards a Phylogeny and Definition of Species at the Molecular Level within the Genus Mycobacterium" 40 Int.J.Sys.Bact. 323, 1990.
Stahl and Urbance, "The Division Between Fast– and Slow– Growing Species Corresponds to Natural Relationships Among the Mycobacterium" 172 J. Bact. 116, 1990.
Killian, "A Taxonomic Study of the Genus Haemophilus, with the Proposal of a New Species" 93 J. Gen. Micro. 9, 1976.
Musser et al. "Genetic Relationships of Serologically Nontypable and Serotype B Strains of *Haemophilus influenzae*" 52 Inf. Imm. 183, 1986.
Malovin et al. "DNA Probe Technology for Rapid Detection of H. influenzae in Clinical Specimens" 26 J. Clin. Micro. 2132, 1988.
Brenner et al "Ten New Species of Legionella" 35 Int. J. Sys. Bact. 50, 1985.
Grimont et al. "DNA Probe Specific for *Legionella pneumophila*" 21 J. Clin. Microbiol. 431 1985.
Festl et al. "DNA Hybridization Probe for the *Pseudomonas fluorescens* Group" 52 Applied and Environmental Micro. 1190, 1986.
Brenner et al "Classification of Ligeionnaires' Disease Bacterium: An Interim Report" 30 Int. J. Sys. Bact. 236, 1980, 1 Bergey's Manual Sys. Bact. 160, 1984.
Carbon et al "The Sequence of 16S rRNA from *Proteus vulgaris*" 9 Nucl. Acid Res. 2325, 1981.
Colwell et al. "Numerical Taxonomy and DNA Reassociation in the Taxonomy of Some Gram–Negative Fermentive Bacteria" 24 Int. J. Sys. Bact. 422, 1974.
Brenner, "Deoxyribonucleic Acid Reassociation in the Taxonomy of Enteric Bacteria" 23 Int J. Sys. Bact. 298, 1973.

(List continued on next page.)

*Primary Examiner*—Carla J. Myers
*Attorney, Agent, or Firm*—Charles B. Cappellari; Carlos A. Fisher

[57] ABSTRACT

Hybridization assay probes specific for *Listeria monocytogenes* and no other Listeria species.

29 Claims, No Drawings

OTHER PUBLICATIONS

Brenner, "Facultatively Anaerobic Gram–Negative Rods", Bergey's Manual of Systemic Bacteriology 408, 1984.

McCarroll et al., "Nucleotide Sequence of the *Dictyostelium discoideum* Small Subunit rRNA . . . " 22 Biochemistry 5858, 1983.

Veldmann et al "The Primary and Secondary Structure of Yeast 26s rRNA" 9 Nucleic Acid Res. 6935, 1981.

Kilpper–Balz et al "Nucleic Acid Hybridization of Group N and Group D Streptococci" 7 Current Microbiology 245, 1982.

Kilpper–Balz and Schleifer, 10 FEMS Microbiology Letters 357, "DNA–rRNA Hybridization Studies Among Staphylococci and Other Gram Positive Bacteria" 1981.

Schleifer and Kilpper–Balz, "Transfer of *Streptococcus faecalis* and *Streptococcus faecium* to the Genus Enterococcus . . . " 34 Int. J. Sys. Bact. 31, 1984.

Harvey and Greenwood, "Relationships Among Catalase–Positive Campylobacters Determined by DNA—DNA Hydribization".

Lau et al. "Phylogenetic Diversity and Position of the Genus Campylobacter" 447 System Appl. Microbiol. 1987.

Baess, "Deoxyribonucleic Acid Relatedness Among Species of Rapidly Growing Mycobacteria" 90 Acta. Path. Microbiol. Imm Scand. Sect. B 371, 1982.

Imaeda, "DNA Relatedness Among Selected Strains of *M. tuberculosis, M. bovis, M. bovis* BCG, *M. microti* and *M. africanum*" 35 Int. J. Sys. Bact. 147, 1985.

Lane et al. "Rapid determination of 16S rRNA squences for phylogenetic analyses" 82 Proc. Natl. Acad. Sci. USA 6955, 1985.

Rogers et al. "Construction of the Mycoplasma Evolutionary Tree from 5S rRNA Sequence Data" 82 Proc. Natl. Acad. Sci. USA 1160, 1985.

Brosius et al., "Complete Nucleotide Sequence of a 16S rRNA Gene from *E. coli*" 75 Proc. Natl. Acad Sci. USA 4801, 1978.

Brosius et al. "Complete Nucleotide Sequence of a 23S rRNA Gene from *E. coli*" 77 Proc. Natl. Acad. Sci. USA 201, 1980.

Weisburg et al. "Eubacterial Origin of Chlamydiae" 197 J. Bacteriology 570, 1986.

Kohne, "Application of DNA Probe Tests to the Diagnosis of Infectious Disease" American Clinical Products Review, Nov. 1986.

Brenner, "DNA Hybridization for the Characterization, Classification, Taxonomy +ID of Bacteria" Impact of Biotechnology on Microbial Detection, Estimation and Characterization, Swaminathan et al. eds. 1986.

Razin, Molecular Biology and Genetics of Mycoplasmas (Mollicutes) 49 Microbiological Reviews 419, 1985.

Crosa et al, "Polynucleotide Sequence Divergence in the Genus Citrobacter" 83 J. Gen. Microbiol. 271, 1974.

"DNA Probes" 9 Clinical Microbiology Newsletter 90, 1987.

Stahl, "Unity in Variety" 4 Biotechnology 623, 1986.

Brenner et al. "Classification of the Legionaires Disease Bacterium: *Legionella pneumophila* . . . " 90 Annals of Internal Medicine 656, 1979.

Ludwig and Stackenbrandt, "A Phylogenetic Analysis of Legionella" 135 Archives of Microbiology 45, 1983.

Brenner et al, "Family Legionellaceae", Current Microbiology 71, 1978.

Kohne et al. "Nucleic Acid Probe Specific for Members of the Genus Legionella" in Thornsbury et al, Legionella Proceedings of the Second International Symposium for Microbiology, Washington 107.

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 28
      (B) TYPE: nucleic acid
      (C) STRANDEDNESS: single
      (D) TOPOLOGY: linear (ii) SEQUENCE DESCRIPTION: SEQ ID NO: 1:

CTGAGAATAG TTTTATGGGA TTAGCTCC      28

(2) INFORMATION FOR SEQ ID NO: 2:

(i) SEQUENCE CHARACTERISTICS:
      (A) LENGTH: 25
      (B) TYPE: nucleic acid
      (C) STRANDEDNESS: single
      (D) TOPOLOGY: linear (ii) SEQUENCE DESCRIPTION: SEQ ID NO: 2:

GGCGAGTTGC AGCCTACAAT CCGAA                                                             25

(2) INFORMATION FOR SEQ ID NO:    3:

(i) SEQUENCE CHARACTERISTICS:
        (A) LENGTH:            28
        (B) TYPE:              nucleic acid
        (C) STRANDEDNESS:      single
        (D) TOPOLOGY:          linear (ii) SEQUENCE DESCRIPTION: SEQ ID NO: 3:

GGAGCUAA UCCCAUAAAA CUAUUCUCAG                                                          28

(2) INFORMATION FOR SEQ ID NO:    4:

(i) SEQUENCE CHARACTERISTICS:
        (A) LENGTH:            28
        (B) TYPE:              nucleic acid
        (C) STRANDEDNESS:      single
        (D) TOPOLOGY:          linear (ii) SEQUENCE DESCRIPTION: SEQ ID NO: 4:

GGAGCTAATC CCATAAAACT ATTCTCAG                                                          28

(2) INFORMATION FOR SEQ ID NO:    5:

(i) SEQUENCE CHARACTERISTICS:
        (A) LENGTH:            28
        (B) TYPE:              nucleic acid
        (C) STRANDEDNESS:      single
        (D) TOPOLOGY:          linear (ii) SEQUENCE DESCRIPTION: SEQ ID NO: 5:

CUGAGAAU AGUUUUAUGG GAUUAGCUCC                                                          28

NUCLEIC ACID PROBES TO *LISTERIA MONOCYTOGENES*

This application is a continuation of application Ser. No. 08/158,168, filed Nov. 24, 1993, now abandoned, which is a continuation of application Ser. No. 07/739,644 filed Aug. 1, 1991, now abandoned.

FIELD OF THE INVENTION

The inventions described and claimed herein relate to the design and construction of nucleic acid probes to *Listeria monocytogenes* which are capable of detecting the organism in test samples of, e.g., sputum, urine, blood and tissue sections, food, soil and water.

BACKGROUND OF THE INVENTION

Two single strands of deoxyribo- ("DNA") or ribo- ("RNA") nucleic acid, formed from nucleotides (including the bases adenine (A), cytosine (C), thymidine (T), guanine (G), uracil (U), or inosine (I)), may associate ("hybridize") to form a double stranded structure in which the two strands are held together by hydrogen bonds between pairs of complementary bases. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs.

When a first single strand of nucleic acid contains sufficient contiguous complementary bases to a second, and those two strands are brought together under conditions which will promote their hybridization, double stranded nucleic acid will result. Under appropriate conditions, DNA/DNA, RNA/DNA, or RNA/RNA hybrids may be formed.

A probe is generally a single stranded nucleic acid sequence which is complementary to some degree to a nucleic acid sequence sought to be detected ("target sequence"). It may be labelled with a detectable moiety such as a radioisotope, antigen or chemiluminescent moiety. A background description of the use of nucleic acid hybridization as a procedure for the detection of particular nucleic acid sequences is described by Kohne, U.S. Pat. No. 4,851,330, and Hogan et al., EPO Patent Application No. PCT/US87/03009, entitled "Nucleic Acid Probes for Detection and/Or Quantitation of Non-Viral Organisms."

Hogan et al., supra, also describes methods for determining the presence of RNA-containing organisms in a sample which might contain such organisms. These methods require probes sufficiently complementary to hybridize to the ribosomal RNA (rRNA) of one or more non-viral organisms or groups of non-viral organisms. The mixture is then incubated under specified hybridization conditions, and assayed for hybridization of the probe and any test sample rRNA.

Hogan et al. also describes probes which detect only specifically targeted rRNA subunit subsequences in particular organisms or groups of organisms in a sample, even in the presence of many non-related organisms, or in the presence of the closest known phylogenetic neighbors. Specific examples of hybridization assay probes are provided for *Mycobacterium avium, Mycobacterium intracellulare, Mycobacterium tuberculosis, Mycobacterium africanum, Mycobacterium bovis, Mycobacterium microti*, the genus Mycobacterium, *Mycoplasma pneumoniae*, the genus Legionella, *Chlamydia trachomatis*, the genus Campylobacter, Enterococcus, the genus Pseudomonas group I, *Enterobacter cloacae, Proteus mirabilis*, the genus Salmonella, *Escherichia coli*, bacteria, fungi, and *Neisseria gonorrhoeae*. Such probe sequences do not cross react with nucleic acids from the groups listed above, or any other bacterial species or infectious agent, under appropriate hybridization stringency conditions.

SUMMARY OF THE INVENTION

This invention discloses and claims novel probes for the detection of *Listeria monocytogenes*. These probes are capable of distinguishing between *Listeria monocytogenes* and its known closest phylogenetic neighbors. These probes detect unique rRNA and gene sequences encoding rRNA, and may be used in an assay for the detection and/or quantitation of *Listeria monocytogenes*.

*Listeria monocytogenes* is a soil-borne organism that has been recognized as a human pathogen for more than 50 years. *Listeria monocytogenes* has been recognized as the etiologic agent of listeriosis, causing meningitis, encephalitis, septicemia, endocarditis, abortion, abscesses and local purulent lesions in humans. (Bertolussi, R., Schlech III, W. F., and W. L. Albritton. 1985. Listeria. *Manual of Clinical Microbiology*, 4th Ed. Lennett, E. H., Balows, A., Hausler, Jr., W. J. and H. J. Shadomy, (Ed.). Pp. 205–208. American Society for Microbiology, Washington D.C. and Gilchrist, M. J. R., 1988. Listeriosis. *Laboratory Diagnosis of Infectious Diseases, Principles and Practice*. Volume 1. Balows, A., Hausler, Jr., W. J., Ohashi, M., and A. Turano Pp. 353–359. Springer-Verlag. New York.) Four major outbreaks of listeriosis within the last decade have been connected to consumption of contaminated food. Pregnant women, neonates, immunocompromised patients and the elderly are at greatest risk for acquiring listeriosis.(Jones, G. L. (Ed.) 1989. *Isolation and Identification of Listeria monocytogenes*. pp. 1–56. U.S.D.H.H.S. Public Health Service, Centers for Disease Control, Atlanta, Ga.)

Current methods for identifying *Listeria monocytogenes* rely upon physiological and biochemical methods. These include gram stain morphology, and tests for catalase, motility, and beta hemolysis on blood agar, and oblique illumination of colonies on blood free agar. (Seeliger, H. P. R., and D. Jones. 1986. Genus Listeria Pirie 1940. *Bergey's Manual of Systematic Bacteriology*. Volume 2. Sneath, P. H. A., Mair, N. S., Sharpe, M. E., and J. G. Holt (Ed.). Pp. 1235–1245. Williams and Wilkins, Baltimore, Md.).

The probes of this invention allow identification of *L. monocytogenes* isolated from culture within 30 minutes of sample preparation.

Thus, in a first aspect, the invention features a hybridization assay probe able to distinguish *Listeria monocytogenes* from other Listeria species.

In preferred embodiments, the probe is complementary to rRNA or rDNA, e.g., a variable region of rRNA; at least 50% of the nucleotides in the oligonucleotide probe are able to hybridize to a contiguous series of bases in at least one variable region of ribosomal nucleic acid in *Listeria monocytogenes*; the probe is a nucleotide polymer able to hybridize to the rRNA of the species *Listeria monocytogenes*; and the oligonucleotide comprises, consists essentially of, or consists of the sequence (SEQ. ID. NO.: 1) CTGAGAAT-AGTTTTATGGGATTAGCTCC or oligonucleotides complementary thereto, with or without a helper probe, as described below.

By "consists essentially of" is meant that the probe is provided as a purified nucleic acid which hybridizes under stringent hybridizing conditions with the desired organism and not with other related organisms. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer able to hybridize to the above oligonucleotides, a nucleic acid hybrid formed with the above oligonucleotides, and a nucleic acid sequence substantially complementary thereto.

The probes of this invention offer a rapid, non-subjective method of identification and quantitation of a bacterial colony for the presence of specific rRNA sequences unique to all strains of *Listeria monocytogenes*.

Other features and advantages of the invention will be apparent from the following description of the preferred embodiments thereof, and from the claims.

DESCRIPTION OF THE PREFERRED EMBODIMENTS

Probes

We have discovered DNA probes complementary to a particular rRNA sequence obtained from *Listeria monocytogenes*. Furthermore, we have successfully used those probes in a specific assay for the detection of *Listeria monocytogenes*, distinguishing *L. monocytogenes* from its known and presumably most closely related taxonomic or phylogenetic neighbors.

With the exception of viruses, all prokaryotic organisms contain rRNA genes encoding 5S rRNA, 16S rRNA and a larger rRNA molecule known as 23S rRNA. Using methods known to those skilled in the art, variable regions of rRNA sequences from the 16S rRNA of *Listeria monocytogenes* were identified as described below. Other such sequences can be identified using equivalent techniques. These methods include partially or fully sequencing the rRNA of *Listeria monocytogenes* and closely related phylogenetic neighbors, aligning the sequences to reveal areas of maximum homology, and examining the alignment for regions with sequence variation. The examples provided below are thus not limiting in this invention.

With respect to sequencing, complementary oligonucleotide primers of about 10–100 bases in length were hybridized to conserved regions in purified rRNA that are specific to the 5S, 16S, or 23S subunits and extended with the enzyme reverse transcriptase. Chemical degradation or dideoxynucleotide-terminated sequencing reactions were used to determine the nucleotide sequence of the extended product. Lane et al., 82 *Proc. Natl. Acad. Sci. USA*, 6955, 1985. In a less preferred method, genomic ribosomal RNA sequences may also be determined by standard procedure.

It is not always necessary to determine the entire nucleic acid. sequence in order to obtain a probe sequence. Extension from any single oligonucleotide primer can yield up to 300–400 bases of sequence. When a single primer is used to partially sequence the rRNA of the target organism and organisms closely related to the target, an alignment can be made as outlined below. If a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Once sequences are aligned it is possible to find the regions in which the primary sequence is variable.

We have identified variable regions by comparative analysis of rRNA sequences both published in the literature and sequences which we have determined. Computers and computer programs which may be used or adapted for the purposes herein disclosed are commercially available. Since the sequence evolution at each of the variable regions (for example, spanning a minimum of 10 nucleotides) is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and %G and %C result in a Tm about 2–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form (i.e., those having at least about 14 out of 17 bases in a contiguous series of bases being complementary); hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes, the differences in these Tm values should be as large as possible (e.g., at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intra-molecular hybrids. By designing a probe so that a substantial portion of the sequence of interest is single stranded, the rate and extent of hybridization may be greatly increased. If the target is the genomic sequence corresponding to the rRNA then it will naturally occur in a double stranded form, this is also the case with the product of the polyaerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone et al., 12 *Nucleic Acids Research* 4051, 1984. Other well-known methods for construction of synthetic oligonucleotides may, of course, be employed. 2 J. Sambrook, E. F. Fritsch and T. Maniatis, *Molecular Cloning* 11 (2d ed. 1989).

Once synthesized, selected oligonucleotide probes may also be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. Isotopic labels include $^3$H, $^{35}$S, $^{32}$P, $^{125}$I, $^{57}$Co and $^{14}$C. Most methods of isotopic labelling involve the use of enzymes and include the known methods of nick translation, end labelling, second strand synthesis, and reverse transcription. When using radiolabelled probes, hybridization can be detected by autoradiography, scintillation counting, or gamma counting. The detection method selected will depend upon the hybridization conditions and the particular radio-isotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. 2 J. Sambrook, E. F. Fritsch and T. Maniatis, *Molecular Cloning*, 11.51 (2d ed. 1989). Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., patent application Ser. No. 613,603 filed Nov. 8, 1990, now U.S. Pat. No. 5,283,174 entitled "Homogeneous Protection Assay," assigned to Gen-Probe Incorporated, Mar. 6, 1992, Reel/Frame 6057/0433-34 hereby incorporated by reference herein.

For Tm measurement using a Hybridization Protection Assay (HPA) the following technique is used. A probe:target hybrid is formed in target excess in a lithium succinate buffered solution containing lithium lauryl sulfate. Aliquots of this hybrid are diluted in the hybridization buffer and incubated for five minutes at various temperatures starting below that of the anticipated Tm (typically 55° C.) and increasing in 2–5 degree increments. This solution is then diluted with a mildly alkaline borate buffer and incubated at a lower temperature (for example 50° C.) for ten minutes. Under these conditions the acridinium ester attached to a single stranded probe is hydrolyzed while that attached to hybridized probe is relatively protected from hydrolysis. The amount of chemiluminescence remaining is proportional to the amount of hybrid, and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which affect relative hybrid stability during thermal denaturation. 2 J. Sambrook, E. F. Fritsch and T. Maniatis, *Molecular Cloning*, 9.51 (2d ed. 1989).

Rate of hybridization may be measured by determining the $C_0t_{1/2}$. The rate at which a probe hybridizes to its target is a measure of the thermal stability of the target secondary structure in the probe region. The standard measurement of hybridization rate is the $C_0t_{1/2}$ which is measured as moles of nucleotide per liter times seconds. Thus, it is the concentration of probe times the time at which 50% of mammal hybridization occurs at that concentration. This value is determined by hybridizing various amounts of probe to a constant amount of target for a fixed time. For example, 0.05 pmol of target is incubated with 0.012, 0.025, 0.05, 0.1 and 0.2 pmol of probe for 30 minutes. The amount of hybrid after 30 minutes is measured by HPA as described above. The signal is then plotted as a log of the percent of maximum Relative Light Units (RLU) (from the highest probe concentration) versus probe concentration (moles of nucleotide per liter). RLU are a measurement of the quantity of photons emitted by the labelled probe measured by the luminometer. The $C_0t_{1/2}$ is found graphically from the concentration corresponding to 50% of maximum hybridization multiplied by the hybridization time in seconds. These values range from $9.0 \times 10^{-6}$ to $9 \times 10^{-5}$ with the preferred values being less than $3.5 \times 10^{-5}$.

As described by Kohne and Kacian (U.S. Ser. No. 816,711 now abandoned, entitled "Accelerated Nucleic Acid Reassociation Method," filed Jan. 7, 1986 abandoned in favor of U.S. application Ser. No. 644,879, filed Jan. 23, 1991, allowed Feb. 7, 1992, assigned to Gen-Probe Incorporated, Apr. 14, 1986, Reel/Frame 4538/0494 hereby incorporated by reference herein, other methods of nucleic acid reassociation can be used.

The following example sets forth synthetic probes complementary to a unique rRNA sequence, or the corresponding gene, from a target organism, *Listeria monocytogenes*, and their use in a hybridization assay.

EXAMPLE

A probe specific for *L. monocytogenes* was identified by sequencing with a primer complementary to the 16S rRNA. The following sequence was characterized and shown to be specific for *Listeria monocytogenes*, Probe 1: 5' CTGAGAATAGTTTTATGGGATTAGCTCC 3'. The phylogenetically near neighbors *L. innocula, L. ivanocii* and *B. thermosphacta* were used as comparisons with the sequence of *L. monocytogenes*.

The above-noted probe is 28 bases in length and hybridizes to the 16S rRNA of *L. monocytogenes*. To demonstrate the reactivity and specificity of the probe for *L. monocytogenes*, it was used in a hybridization assay. The probe was first synthesized with a non-nucleotide linker, then labelled with a chemiluminescent acridinium ester as described in EPO Patent Application No. PCT/US88/03361, entitled "Acridinium Ester Labeling and Purification of Nucleotide Probes filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled-probe measured by the luminometer. The conditions of hybridization, hydrolysis and detection are described in Arnold, et al., 35 *Clin. Chem.* 1588, 1989.

Nucleic acid hybridization was enhanced by the use of "Helper Probes" as disclosed in Hogan et al., U.S. Pat. No. 5,030,557, entitled "Means and Methods for Enhancing Nucleic Acid Hybridization", issued Jul. 9, 1991, and hereby incorporated by reference herein. RNA was hybridized to the acridinium ester-labeled probe in the presence of an unlabeled Helper Probe, oligonucleotide SEQ. ID. NO. 2 with the sequence of 5' GGCGAGTTGCAGCCTACAATC-CGAA 3'.

In the following experiment, RNA released from one colony or $>10^8$ organisms was assayed. An example of such a method is provided by Murphy et al., U.S. Ser. No. 841,860, now abandoned entitled "Method for Releasing RNA and DNA from Cells", filed Mar. 20, 1986, abandoned in favor of U.S. Ser. No. 298,765, filed Jan. 17, 1989 abandoned in favor of U.S. Ser. No. 711,114, filed Jun. 21, 1991, assigned to Gen-Probe Incorporated, May 23, 1986, Reel/Frame 4566/0901, hereby incorporated by reference herein. An RLU value greater than 30,000 RLU is a positive reaction; less than 30,000 is a negative reaction.

The following data show that the probes did not cross react with organisms from a wide phylogenetic cross section. These ATCC isolates were tested in duplicate, the RLU given is the average of the duplicates

| ATCC NO. | ORGANISM | AVE RLU | RESULT |
| --- | --- | --- | --- |
| 33604 | *Acinetobacter calcoaceticus* | 1030 | – |
| 15309 | *Acinetobacter lwoffii* | 1857 | – |
| 19411 | *Actinomyces pyogenes* | 2959 | – |
| 11563 | *Aerococcus viridans* | 1267 | – |
| 7966 | *Aeromonas hydrophila* | 2100 | – |
| 27061 | *Alcaligenes denitrificans xylosoxydans* | 842 | – |
| 8750 | *Alcaligenes faecalis* | 1507 | – |
| 9345 | *Arcanobacterium haemolyticum* | 4281 | – |
| 8246 | *Bacilius brevis* | 1117 | – |
| 6051 | *Bacillus subtilis* | 2350 | – |
| 23745 | *Bacteroides fragilis* | 1214 | – |
| 10580 | *Bordetella bronchiseptica* | 1044 | – |
| 25238 | *Branhamella catarrhalis* | 1302 | – |
| 9172 | *Brevibacterium linens* | 2585 | – |
| 11509 | *Brochothrix thermosphacta* | 3118 | – |
| 33560 | *Camplyobacter jejuni* | 1046 | – |
| 18804 | *Candida albicans* | 672 | – |
| 27872 | *Capnocytophaga ochracea* | 836 | – |
| 29094 | *Chromobacterium violaceum* | 1500 | – |
| 14501 | *Clostridium innocuum* | 898 | – |
| 13124 | *Clostridium perfringens* | 1493 | – |
| 11913 | *Corynebacterium diphtheriae* | 1107 | – |
| 10700 | *Corynebacterium pseudodiphtheriticum* | 829 | – |
| 19410 | *Corynebacterium pseudotuberculosis* | 856 | – |
| 373 | *Corynebacterium xerosis* | 1763 | – |
| 32045 | *Crytococcus neoformans* | 1542 | – |
| 35073 | *Deinococcus radiodurans* | 1758 | – |
| 15994 | *Derxia gummosa* | 2681 | – |
| 19433 | *Enterococcus faecalis* | 1340 | – |
| 19434 | *Enterococcus faecium* | 2357 | – |
| 19414 | *Erysipelothrix rhusiopathiae* | 891 | – |
| 10798 | *Escherichia coli* | 1827 | – |
| 13253 | *Flavobacterium meningosepticum* | 2175 | – |
| 10379 | *Gemella haemolysans* | 3500 | – |
| 19418 | *Haemophilus influenzae* | 1472 | – |
| 23357 | *Klebsiella pneumoniae* | 1099 | – |
| 33403 | *Kurthia zopfii* | 990 | – |
| 4356 | *Lactobacillus acidophilus* | 1137 | – |
| 14869 | *Lactobacillus brevis* | 3083 | – |

-continued

| ATCC NO. | ORGANISM | AVE RLU | RESULT |
|---|---|---|---|
| 25258 | Lactobacillus jensenii | 1061 | − |
| 19257 | Lactococcus lactis cremoris | 1849 | − |
| 11454 | Lactococcus lactis lactis | 1440 | − |
| 33152 | Legionella pneumophila | 2669 | − |
| 33313 | Leuconostoc paramesenteroides | 1810 | − |
| 19120 | Listeria grayi | 1343 | − |
| F4085 | Listeria grayi | 1036 | − |
| F4078 | Listeria innocua | 945 | − |
| 19119 | Listeria ivanovii | 1395 | − |
| F4081 | Listeria ivanovii | 1339 | − |
| 35152 | Listeria monocytogenes | 823760 | + |
| 15313 | Listeria monocytogenes | 809571 | + |
| F4235 | Listeria monocytogenes 1/2a | 633247 | + |
| F4260 | Listeria monocytogenes 1/2b | 558218 | + |
| F6262 | Listeria monocytogenes 1/2c | 808860 | + |
| 19113 | Listeria monocytogenes 3 | 435338 | + |
| F2365 | Listeria monocytogenes 4b | 944800 | + |
| F4076 | Listeria murrayi | 1192 | − |
| F4088 | Listeria seeligeri | 1895 | − |
| F4082 | Listeria welshimeri | 1450 | − |
| 27570 | Micrococcus kristinae | 779 | − |
| 4698 | Micrococcus luteus | 2534 | − |
| 14470 | Mycobacterium gordonae | 1403 | − |
| 25177 | Mycobacterium tuberculosis | 673 | − |
| 23114 | Mycoplasma hominis | 680 | − |
| 15531 | Mycoplasma pneumoniae | 624 | − |
| 13077 | Neisseria meningitidis | 1549 | − |
| 19247 | Nocardia asteroides | 1466 | − |
| 33225 | Oerskovia turbata | 5060 | − |
| 27402 | Oerskovia xanthineolytica | 1535 | − |
| 17741 | Paracoccus denitrificans | 1208 | − |
| 33314 | Pediococcus acidilactici | 872 | − |
| 27337 | Peptostreptococcus anaerobius | 1069 | − |
| 14955 | Peptostreptococcus magnus | 1040 | − |
| 6919 | Proprionibacterium acnes | 860 | − |
| 25933 | Proteus mirabilis | 4098 | − |
| 25330 | Pseudomonas aeruginosa | 1320 | − |
| 33071 | Rahnella aquatilis | 963 | − |
| 25592 | Rhodococcus bronchialis | 2067 | − |
| 11170 | Rhodospirillum rubrum | 1513 | − |
| 12598 | Staphylococcus aureus | 973 | − |
| 12228 | Staphylococcus epidermidis | 914 | − |
| 13813 | Streptococcus agalactiae | 1969 | − |
| 33317 | Streptococcus bovis | 2107 | − |
| 27957 | Streptococcus dysgalactiae | 1524 | − |
| 9812 | Streptococcus equinus | 1563 | − |
| 9811 | Streptococcus mitis | 1214 | − |
| 25175 | Streptococcus mutans | 1011 | − |
| 6306 | Streptococcus pneumoniae | 962 | − |
| 19615 | Streptococcus pyogenes | 1829 | − |
| 13419 | Streptococcus salivarius | 927 | − |
| 10556 | Streptococcus sanguis | 1444 | − |
| 27958 | Streptococcus uberis | 848 | − |
| 23345 | Streptomyces griseus | 2320 | − |
| 17802 | Vibrio parahaemolyticus | 1457 | − |
| 9610 | Yersinia enterocolitica | 875 | − |

The above data confirm that the novel probes herein disclosed and claimed are capable of distinguishing *Listeria monocytogenes* from its known nearest phylogenetic neighbors.

Other embodiments are within the following claims.

I claim:

1. A probe mix comprising:
   a) a nucleic acid hybridization assay probe which detects the presence of *Listeria monocytogenes* comprising an oligonucleotide 15 to 100 bases in length having at least 14 out of 17 contiguous bases perfectly complementary to a *Listeria monocytogenes* nucleic acid variable region, said variable region consisting of a nucleic acid sequence selected from the group consisting of:
      5' CTGAGAATAGTTTTATGGGATTAGCTCC (SEQ ID NO: 1), and
      5' GGAGCTAATCCCATAAAACTATTCTCAG (SEQ ID NO: 4);
         wherein under stringent conditions said probe hybridizes to *Listeria monocytogenes* 16S rRNA or rDNA to form a detectable probe:target duplex, but said probe does not hybridize to non-target nucleic acid from *Listeria grayi, Listeria innocua, Listeria ivanovii, Listeria murrayi, Listeria seeligeri, Listeria welshimeri* and *Brochothrix thermosphacta* to form a detectable probe:non-target duplex; and
   b) a helper probe comprising a nucleotide base sequence selected from the group consisting of: 5' GGCGAGTTGCAGCCTACAATCCGAA (SEQ ID NO: 2), and the RNA version thereof.

2. The probe mix of claim 1, wherein said hybridization probe is 28 to 50 bases in length comprising a nucleotide base sequence selected from the group consisting of:
   5' CTGAGAATAGTTTTATGGGATTAGCTCC (SEQ ID NO: 1),
   5' GGAGCUAAUCCCAUAAAACUAUUCUCAG (SEQ ID NO: 3),
   5' GGAGCTAATCCCATAAAACTATTCTCAG (SEQ ID NO: 4), and
   5' CUGAGAAUAGUUUUAUGGGAUUAGCUCC (SEQ ID NO: 5).

3. The probe mix of claim 2, wherein said hybridization probe consists of said nucleotide base sequence.

4. The probe mix of claim 3, wherein said helper probe consists of said helper nucleotide base sequence.

5. A method for detecting whether *Listeria monocytogenes* may be present in a sample comprising the steps of:
   a) providing to said sample a nucleic acid hybridization assay probe comprising an oligonucleotide having at least 14 out of 17 contiguous bases perfectly complementary to a *Listeria monocytogenes* nucleic acid variable region, said variable region consisting of a nucleic acid sequence selected from the group consisting of;
      5' CTGAGAATAGTTTTATGGGATTAGCTCC (SEQ ID NO: 1), and
      5' GGAGCTAATCCCATAAAACTATTCTCAG (SEQ ID NO: 4);
         wherein under stringent hybridization conditions said probe hybridizes to *Listeria monocytogenes* 16S rRNA or rDNA to form a detectable probe-:target duplex, but said probe does not hybridize to non-target nucleic acid from *Listeria grayi, Listeria innocua, Lysteria ivanovii, Listeria murrayi, Listeria seeligeri, Listeria welshimeri* and *Brochothrix thermosphacta* to form a detectable probe:non-target duplex; and
   b) detecting the formation of said detectable probe:target duplex as an indication that *Listeria monocytogenes* may be present in said same.

6. The method of claim 5, wherein said probe is 28 to 50 nucleotides in length comprising a nucleic acid sequence selected from the group consisting of:
   5' CTGAGAATAGTTTTATGGGATTAGCTCC (SEQ ID NO: 1),
   5' GGAGCUAAUCCCAUAAAACUAUUCUCAG (SEQ ID NO: 3),
   5' GGAGCTAATCCCATAAAACTATTCTCAG (SEQ ID NO: 4), and
   5' CUGAGAAUAGUUUUAUGGGAUUAGCUCC (SEQ ID NO: 5).

7. The method of claim 6, wherein said probe said consists of said nucleic acid sequence.

8. A nucleic acid hybridization assay probe for specifically detecting the presence of *Listeria monocytogenes*, said probe having a nucleotide base sequence selected from the group consisting of:
   5' CTGAGAATAGTTTTATGGGATTAGCTCC (SEQ ID NO: 1),
   5' GGAGCUAAUCCCAUAAAACUAUUCUCAG (SEQ ID NO: 3),
   5' GGAGCTAATCCCATAAAACTATTCTCAG (SEQ ID NO: 4), and
   5' CUGAGAAUAGUUUUAUGGGAUUAGCUCC (SEQ ID NO: 5);
      wherein under stringent conditions said probe hybridizes to *Listeria monocytogenes* 16S rRNA or rDNA to form a detectable probe:target duplex, but said probe does not hybridize to non-target nucleic acid from *Listeria grayi, Listeria innocua, Listeria ivanovii, Listeria murrayi, Listeria seeligeri, Listeria welshimeri* and *Brochothrix thermosphacta* to form a detectable probe:non-target duplex.

9. The nucleic acid probe of claim 8, wherein said probe is labeled with a detectable moiety.

10. The nucleic acid probe of claim 9, wherein said detectable moiety is selected from the group consisting of: radioisotope, fluorescent molecule, chemiluminescent molecule, enzyme, cofactor and hapten.

11. The nucleic acid probe of claim 9, wherein said detectable moiety is an acridinium ester.

12. The nucleic acid probe of claim 9, wherein said detectable moiety is attached to said probe at the site of a base mismatch with a polynucleotide sequence of at least one of *Listeria grayi, Listeria innocua, Listeria ivanovii, Listeria murrayi, Listeria seeligeri, Listeria welshimeri* and *Brochothrix thermosphacta*.

13. The nucleic acid probe of claim 12, wherein said detectable moiety is an acridinium ester.

14. A nucleic acid hybrid for facilitating detection of *Listeria monocytogenes* comprising:
   a) a nucleic acid hybridization assay probe which specifically detects the presence of said *Listeria monocytogenes*, said probe having a nucleotide base sequence selected from the group consisting of:
      5' CTGAGAATAGTTTTATGGGATTAGCTCC (SEQ ID NO: 1),
      5' GGAGCUAAUCCCAUAAAACUAUUCUCAG (SEQ ID NO: 3),
      5' GGAGCTAATCCCATAAAACTATTCTCAG (SEQ ID NO: 4), and
      5' CUGAGAAUAGUUUUAUGGGAUUAGCUCC (SEQ ID NO: 5);
         wherein under stringent conditions said probe hybridizes to *Listeria monocytogenes* 16S rRNA or rDNA to form a detectable probe:target duplex, but said probe does not hybridize to non-target nucleic acid from *Listeria grayi, Listeria innocua, Listeria ivanovii, Listeria murrayi, Listeria seeligeri, Listeria welshimeri* and *Brochothrix thermosphacta* to form a detectable probe:non-target duplex; and
   b) *Listeria monocytogenes* 16S rRNA or rDNA.

15. The nucleic acid hybrid of claim 14, wherein said probe is labeled with a detectable moiety.

16. The nucleic acid hybrid of claim 14, wherein said detectable moiety is selected from the group consisting of: radioisotope, fluorescent molecule, chemiluminescent molecule, enzyme, cofactor and hapten.

17. The nucleic acid hybrid of claim 14, wherein said detectable moiety is an acridinium ester.

18. The nucleic acid hybrid of claim 14, wherein said detectable moiety is attached to said probe at the site of a base mismatch with a polynucleotide sequence of at least one of *Listeria grayi, Listeria innocua, Listeria ivanovii, Listeria murrayi, Listeria seeligeri, Listeria welshimeri* and *Brochothrix thermosphacta*.

19. The nucleic acid hybrid of claim 17, wherein said detectable moiety is an acridinium ester.

20. The nucleic acid probe of claim 4, wherein said probe is labeled with a detectable moiety.

21. The nucleic acid probe of claim 19, wherein said detectable moiety is selected from the group consisting of: radioisotope, fluorescent molecule, chemiluminescent molecule, enzyme, cofactor and hapten.

22. The nucleic acid probe of claim 19, wherein said detectable moiety is an acridinium ester.

23. The nucleic acid probe of claim 19, wherein said detectable moiety is attached to said probe at the site of a base mismatch with a polynucleotide sequence of at least one of *Listeria grayi, Listeria innocua, Listeria ivanovii, Listeria murrayi, Listeria seeligeri, Listeria welshimeri* and *Brochothrix thermosphacta*.

24. The nucleic acid probe of claim 22, wherein said detectable moiety is an acridinium ester.

25. The nucleic acid probe of claim 7, wherein said probe is labeled with a detectable moiety.

26. The nucleic acid probe of claim 24, wherein said detectable moiety is selected from the group consisting of: radioisotope, fluorescent molecule, chemiluminescent molecule, enzyme, cofactor and hapten.

27. The nucleic acid probe of claim 24, wherein said detectable moiety is an acridinium ester.

28. The nucleic acid probe of claim 24, wherein said detectable moiety is attached to said probe at the site of a base mismatch with a polynucleotide sequence of at least one of *Listeria grayi, Listeria innocua, Listeria ivanovii, Listeria murrayi, Listeria seeligeri, Listeria welshimeri* and *Brochothrix thermosphacta.*

29. The nucleic acid probe of claim 27, wherein said detectable moiety is an acridinium ester.

* * * * *

UNITED STATES PATENT AND TRADEMARK OFFICE
CERTIFICATE OF CORRECTION

PATENT NO : 6,028,187
DATED : FEBRUARY 22, 2000
INVENTOR(S) : HOGAN, J.

It is certified that error appears in the above-identified patent and that said Letters Patent is hereby corrected as shown below:

In claim 2, line 2, replace "comprising" with --and comprises--.

In claim 6, line 2, replace "nucleotides" with --bases-- , and replace "comprising a nucleic acid" with --and comprises a nucleotide base--.

In claim 7, line 1, delete second appearance of "said"; and line 2, replace "nucleic acid" with --nucleotide base--.

In claim 16, line 1, replace "claim 14" with --claim 15--.

In claim 17, line 1, replace "claim 14" with --claim 15--.

In claim 18, line 1, replace "claim 14" with --claim 15--.

In claim 19, line 1, replace "claim 17" with --claim 18--.

In claim 20, line 1, replace "nucleic acid probe" with --probe mix--, and replace "claim 4" with --claim 3--.

In claim 21, line 1, replace "nucleic acid probe " with --probe mix--, and replace "claim 19" with --claim 20--.

In claim 22, line 1, replace "nucleic acid probe" with --probe mix--, and replace "claim 19" with --claim 20--.

In claim 23, line 1, replace "nucleic acid probe" with --probe mix--, and replace "claim 19" with --claim 20--.

UNITED STATES PATENT AND TRADEMARK OFFICE
CERTIFICATE OF CORRECTION

PATENT NO  : 6,028,187
DATED      : FEBRUARY 22, 2000
INVENTOR(S): HOGAN, J.

It is certified that error appears in the above-identified patent and that said Letters Patent is hereby corrected as shown below:

In claim 24, line 1, replace "nucleic acid probe" with --probe mix--, and replace "claim 22" with --claim 23--.

In claim 25, line 1, replace "nucleic acid probe" with --method--.

In claim 26, line 1, replace "nucleic acid probe" with --method--, and replace "claim 24" with --claim 25--.

In claim 27, line 1, replace "nucleic acid probe" with --method--, and replace "claim 24" with --claim 25--.

In claim 28, line 1, replace "nucleic acid probe" with --method--, and replace "claim 24" with --claim 25--.

In claim 29, line 1, replace "nucleic acid probe" with --method--, and replace "claim 27" with --claim 28--.

Signed and Sealed this

Twentieth Day of March, 2001

*Attest:*

NICHOLAS P. GODICI

*Attesting Officer*    *Acting Director of the United States Patent and Trademark Office*